(12) United States Patent
Hansson

(10) Patent No.: US 6,547,564 B1
(45) Date of Patent: Apr. 15, 2003

(54) BONE IMPLANT HAVING CIRCUMFERENTIALLY ORIENTED ROUGHNESS

(75) Inventor: Stig Hansson, Askim (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/402,918

(22) PCT Filed: Jul. 14, 1999

(86) PCT No.: PCT/SE99/01272

§ 371 (c)(1),
(2), (4) Date: Oct. 13, 1999

(87) PCT Pub. No.: WO00/03657

PCT Pub. Date: Jan. 27, 2000

(30) Foreign Application Priority Data

Jul. 17, 1998 (SE) .................................................. 9802571

(51) Int. Cl.[7] .............................................. A61C 8/00
(52) U.S. Cl. .......................... 433/174; 606/60; 606/65; 606/72; 606/73; 623/11.11; 623/23.5
(58) Field of Search ........................ 433/174, 225, 433/172, 173, 175; 606/73, 61, 65, 72; 623/16.11, 11.11, 23.5

(56) References Cited

U.S. PATENT DOCUMENTS

| | | | | |
|---|---|---|---|---|
| 4,781,591 A | | 11/1988 | Allen | 433/174 |
| 4,854,311 A | * | 8/1989 | Steffee | 128/92 |
| 5,076,788 A | | 12/1991 | Niznick | 433/173 |
| 5,078,607 A | | 1/1992 | Niznick | 433/174 |
| 5,087,199 A | * | 2/1992 | Lazarof | 433/173 |
| 5,259,398 A | * | 11/1993 | Vrespa | 128/898 |
| 5,302,126 A | | 4/1994 | Wimmer | 433/173 |
| 5,376,004 A | | 12/1994 | Mena | 433/173 |
| 5,427,527 A | | 6/1995 | Niznick et al. | 433/174 |
| 5,435,723 A | | 7/1995 | O'Brien | 433/174 |
| 5,527,183 A | | 6/1996 | O'Brien | 433/174 |
| 5,571,017 A | | 11/1996 | Niznick | 433/174 |
| 5,588,838 A | | 12/1996 | Hansson et al. | 433/173 |
| 5,601,429 A | | 2/1997 | Blacklock | 433/174 |
| 5,601,553 A | * | 2/1997 | Trebing et al. | 606/61 |
| 5,607,428 A | * | 3/1997 | Lin | 606/69 |
| 5,727,943 A | | 3/1998 | Beaty et al. | 433/174 |
| 5,954,722 A | * | 9/1999 | Bono | 606/61 |
| 6,045,554 A | * | 4/2000 | Grooms et al. | 606/73 |
| 6,231,606 B1 | * | 5/2001 | Graf et al. | 623/13 |
| 6,299,615 B1 | * | 10/2001 | Huebner | 606/73 |

FOREIGN PATENT DOCUMENTS

| | | |
|---|---|---|
| EP | 0424734 | 5/1991 |
| TW | 239291 | 1/1995 |
| WO | 9417750 | 8/1994 |
| WO | 9743976 | 11/1997 |

* cited by examiner

Primary Examiner—Corrine McDermott
Assistant Examiner—Urmi Chattopadhyay
(74) Attorney, Agent, or Firm—White & Case LLP

(57) ABSTRACT

Implant (10) having a shaft which is adapted in use to be embedded in bone tissue and which has an outer surface provided with a circumferentially-oriented roughness. The circumferentially-oriented roughness has first and second axial sections (19, 21) with each section comprising a series of circumferentially-oriented peaks which have a crest and which are axially spaced apart by troughs. The axial spacing (d) between the crests of adjacent peaks in the first axial section (19) is less than the axial spacing (3d) between the crests of adjacent peaks in the second axial section (21). Although the axial spacing between the crests of adjacent peaks in the first and second axial sections of circumferentially-oriented roughness differs, the first and second axial sections of circumferentially-oriented roughness are adapted in use to provide the same or substantially the same pitch.

82 Claims, 4 Drawing Sheets

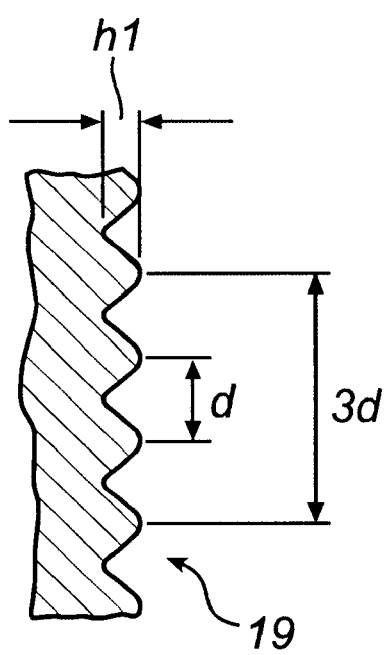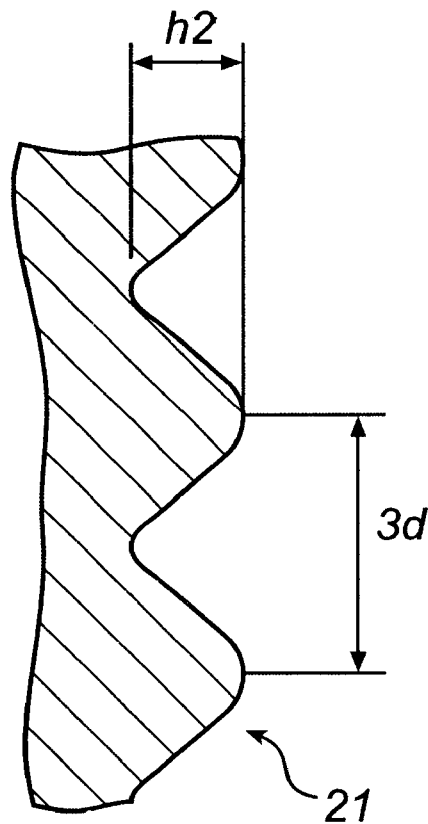
Fig. 6                    Fig. 7

BONE IMPLANT HAVING CIRCUMFERENTIALLY ORIENTED ROUGHNESS

FIELD OF THE INVENTION

The present invention relates to an implant having a shaft which is adapted in use to be embedded in bone tissue and which has an outer surface provided with a circumferentially-oriented roughness. This will hereinafter be referred to as an "implant of the type defined".

BACKGROUND OF THE INVENTION

Implants of the type defined are known for use as the anchoring members of dental and orthopaedic prostheses. To this end, the implant is inserted into a bore-hole drilled into the bone tissue of a bone tissue structure at a site where a prosthesis is required, ordinarily by screwing of the implant into the bore-hole. The convention in the art is for the circumferentially-oriented roughness to take the form of a screw thread and in this case the bore-hole will ordinarily be (i) provided with internal threads in advance, or (ii) left untapped with the implant being provided with a self-tapping capacity, e.g. by the provision of one or more axially-extending cutting recesses or notches in the screw thread.

A superstructure having the prosthetic part of the prosthesis is then secured to the implant. In the case of a dental prosthesis, the superstructure will typically consist of a spacer or transmucosal component which engages to the implant to bridge the gingiva overlying the maxilla or mandible at the implant site and the prosthetic part, e.g. a crown, bridge or denture, is then secured to the spacer. There are various other forms that the superstructure can take as is known in the art. For instance, the prosthetic part may be secured directly to the implant.

The long-term integrity of the prosthesis is highly dependent on the successful osseointegration of the implant with the bone tissue structure, that is to say, the remodelling of the bone tissue in the bone tissue structure into direct apposition with the implant. A study on the factors which affect the osseointegration of implants was undertaken by Professor Per-Ingvar Brånemark and co-workers and the results were published in a book entitled *Osseointegrated Implants in the Treatment of the Edentulous law: Experience from a 10-Year Period*, Almqvist & Wiskell International. Stockholm, Sweden, 1977. It was found by Brånemark et al that successful osseointegration depends upon inter alia the use of biocompatible materials for the implant, for example titanium and alloys thereof, and the surgical procedure adopted, for example leaving the implant unloaded for several months before adding the superstructure. Implants of the type defined are not necessarily always used as part of a prosthesis, in some instances they can be a "stand alone" structure. As an example, implants of the type defined are known for use as bone fixation screws. The success of these "stand alone" implants is also highly dependent on their successful osseointegration.

Implants of the type defined have some notable advantages in promoting successful osseointegration with the adjacent bone tissue, a major one being as a result of the fact that the main loads on the implant in the clinical situation are axial loads. These implants are very well suited to support axial loads and this may be particularly important in the initial stages of the osseointegration process in which it is important that the implant is fully stable and as immovable as possible in the bore-hole (primary fixation). One can consider this to be due to the bone tissue growing into the troughs between adjacent peaks of the circumferentially-oriented roughness on the implant.

The Applicant has also identified that it is advantageous for an implant of the type defined to transmit the axial loading thereon evenly to the adjacent bone tissue to prevent high stress concentrations occurring in the adjacent bone tissue and concomitantly marginal bone tissue resorption. If marginal bone tissue resorption occurs this will reduce the anchorage of the implant and may undermine the long term stability of the implant resulting in due course in failure of the prosthesis. In the particular case of dental prostheses, the aesthetic appeal is also undermined by marginal bone tissue resorption, an important drawback since dental prosthetics forms part of the field of cosmetic surgery.

The present invention proposes to provide an implant of the type defined having features which promote its maintenance in a bone tissue structure whilst at the same time facilitating its insertion into the bone tissue structure in the first place.

SUMMARY OF THE INVENTION

According to the present invention there is provided an implant of the type defined in which the circumferentially-oriented roughness has first and second axial sections each comprising a series of circumferentially-oriented peaks which have a crest and which are axially spaced apart by troughs, the axial spacing between the crests of adjacent peaks in the first axial section is less than the axial spacing between the crests of adjacent peaks in the second axial section and the first and second axial sections of circumferentially-oriented roughness are adapted in use to provide the same or substantially the same pitch.

The larger inter-peak spacing in the second axial section of circumferentially-oriented roughness acts to promote primary fixation of the implant in the bone tissue during the early phases of osseointegration since each trough between adjacent peaks can capture a relatively large volume of bone tissue to interlock the implant with the bone tissue. The smaller inter-peak spacing in the first axial section, on the other hand, enables the stiffness of the implant to be increased thereby improving the ability of the implant to transmit loads more evenly to the bone tissue to inhibit marginal bone resorption. Adapting the first and second axial sections to have the same or substantially the same pitch means that both axial sections produce the same or substantially the same axial displacement into the bone tissue on one rotation thereof thus ensuring that the provision of the two different axial sections of circumferentially-oriented roughness does not complicate insertion of the implant into the bone tissue. If the first and second axial sections of circumferentially-oriented roughness did not have the same or substantially the same pitch then a greater force would need to be applied to insert the implant resulting in fractures being formed in the bone tissue.

In an embodiment of the invention such as the one hereinafter to be described the pitch is a predetermined distance, the ratio of the predetermined distance to the axial spacing between the crests of adjacent peaks in the first axial section is a first multiple integer and the ratio of the predetermined distance to the axial spacing between the crests of adjacent peaks in the second axial section is a second multiple integer which is less than the first multiple integer. The first multiple integer may be a multiple integer of the second multiple integer.

In an embodiment of the invention such as the one hereinafter to be described the peaks in the first and second axial sections are circumferentially-oriented at a common inclined angle to the main axis of the implant.

In an embodiment of the invention such as the one hereinafter to be described the shaft has a coronal end and an apical end and the first axial section is located coronally of the second axial section.

In an embodiment of the invention such as the one hereinafter to be described the first and second axial sections are contiguous.

In an embodiment of the invention such as the one hereinafter to be described the first axial section extends from the coronal end of the shaft to a position coronally of the apical end and the second axial section extends from the first axial section towards the apical end of the shaft. The implant may have a coronal end which is spaced coronally from the coronal end of the shaft by a smooth coronal portion of the implant, as in the embodiment of the invention hereinafter to be described, in which case the smooth coronal portion is preferably no more than 4% of the total length of the implant, more preferably in the range 1.5–3.7% of said total length.

In an embodiment of the invention such as the one hereinafter to be described the axial extent of the first axial section is greater than the axial extent of the second axial section. Alternatively, the axial extent of the first axial section may be less than the axial extent of the second axial section or the axial extents of the first and second axial sections may be the same or substantially the same.

In an embodiment of the invention in which the first axial section is disposed coronally of the second axial section, such as the one hereinafter to be described, a blind bore extends apically into the shaft from the coronal end thereof to an end surface in-between the apical and coronal ends of the shaft for a superstructure to be secured to the implant, the blind bore comprising an internally-threaded section having a coronal edge and an apical edge for screw connection of the superstructure to the implant with the apical edge terminating at a position which is disposed apically of the first axial section. Alternately, the apical edge of the internally-threaded section of the blind bore may terminate at a position which is disposed coronally of the second axial section. The internally-threaded section may be an apical section of the blind bore, as in the embodiment of the invention hereinafter to be described.

In an embodiment of the invention such as the one hereinafter to be described all or substantially all of the crests of the peaks in the first and second axial sections lie on an axial plane parallel to the main axis of the shaft. Expressed another way, the major transverse dimension of the implant at the first and second axial sections is uniform.

In an embodiment of the invention such as the one hereinafter to be described the height of the peaks, as measured from the troughs to the crests, in the first axial section differs from that in the second axial section. To advantage, the height of the peaks in the first axial section is less than that in the second axial section. This feature further enables the stiffness of the implant to be increased.

In an alternative embodiment of the invention the height of the peaks, as measured from the troughs to the crests, in the first axial section is the same or substantially the same as in the second axial section.

In an embodiment of the invention such as the one hereinafter to be described the ratio of the height of the peaks, as measured from the troughs to the crests, to the axial spacing between the crests of adjacent peaks in the first axial section is the same or substantially the same as in the second axial section.

In an embodiment of the invention such as the one hereinafter to be described the height of the peaks, as measured from the troughs to the crests, in the first axial section is no greater than 0.2 mm, for example in the range 0.02–0.20 mm, and the height of the peaks, as measured from the troughs to the crests, in the second axial section is greater than that in the first axial section, for instance in the range 0.15 mm to 1 mm. Such heights complement the primary fixation and stiffness characteristics of the implant provided by the different inter-peak spacings of the first and second axial sections.

In an embodiment of the invention such as the one hereinafter to be described the peaks in the first and second axial sections are bounded by flank surfaces and the angle between the opposed flanks of adjacent peaks in the first and second axial sections is the same.

In an embodiment of the invention such as the one hereinafter to be described the troughs in at least one of the first and second axial sections are a continuous curved surface.

In an embodiment of the invention such as the one hereinafter to be described the circumferentially-oriented roughness in the first and/or second axial section is presented by a screw thread profile with the circumferentially-oriented peaks being defined by thread elements of the screw thread profile.

Typically, the screw thread profile of the first and/or second axial section will be formed by a screw thread structure. In such case, the screw thread structure of the first axial section may be formed by a first set of independent screw threads each having turns; the turns of each independent screw thread in the first set defining thread elements in the first axial section and being sequentially arranged with the turns of the other independent screw threads in the first set with adjacent turns of one of the independent screw threads of the first set being axially-spaced apart by a predetermined spacing distance which is the same for adjacent turns of the other independent screw threads in the first set; and the screw thread structure of the second axial section may be formed by (i) an independent screw thread having turns which define the thread elements of the second axial section and are axially-spaced apart by the predetermined spacing distance or essentially the predetermined spacing distance, or (ii) a second set of independent screw threads numbering less than in the first set each having turns, the turns of each independent screw thread in the second set defining thread elements in the second axial section and being sequentially arranged with the turns of the other independent screw threads in the second set with adjacent turns of each independent screw thread of the second set being axially-spaced apart by the predetermined spacing distance or essentially the predetermined spacing distance.

In an embodiment of the invention one or more of the independent screw threads of the first and second axial sections are shared by the first and second axial sections.

In an embodiment of the invention such as the one hereinafter to be described the or each independent screw thread of at least one of the first and second axial sections is a microthread, that is to say, a thread having a height which is no greater than 0.2 mm.

In an embodiment of the invention only the screw threads of the first axial section are microthreads. It could be the case, though, that the screw threads of both the first and second axial sections are microthreads.

In an embodiment of the invention the circumferentially-oriented roughness in at least one of the first and second axial sections is formed by a series of axially spaced-apart cirucmferential lines of beads. The beads in each line may be circumferentially spaced-apart.

In an embodiment of the invention such as the one hereinafter to be described the implant is a dental implant adapted for implantation in the maxilla or mandible of an edentulous patient for supporting a superstructure which presents one or more artificial teeth.

According to the invention there is further provided a method of implanting an implant into a bone tissue structure comprising the steps of providing an implant according to the invention, providing a bore-hole in the bone tissue structure and screwing the implant into the bore-hole so that the shaft is embedded in the bone tissue.

BRIEF DESCRIPTION OF THE DRAWINGS

By way of example, a self-tapping endosseous screw-type dental implant in accordance with the present invention will now be described with reference to the accompanying Figures of drawings in which:

FIG. 6 is an exploded view of a first section of the external screw threading on the dental implant; and FIG. 7 is an exploded view of a second section of the external screw threading on the dental implant.

DESCRIPTION OF EXEMPLARY EMBODIMENT OF THE INVENTION

In the accompanying Figures of drawings there is shown various views of a self tapping endosseous screw-type dental implant 10 of a dental prosthesis in accordance with the present invention. The implant 10 is for insertion into a bore-hole drilled into a toothless-site in a maxilla or mandible of a partially or fully edentulous patient to anchor to the maxilla or mandible a superstructure of the prosthesis which comprises a prosthetic part, namely one or more artificial teeth. The implant 10 is made from commercially pure titanium, a titanium alloy, another biocompatible metal or metal alloy or a ceramic to promote osseointegration of the implant with the bone tissue of the boundary walls of the bore-hole.

Figure 1:
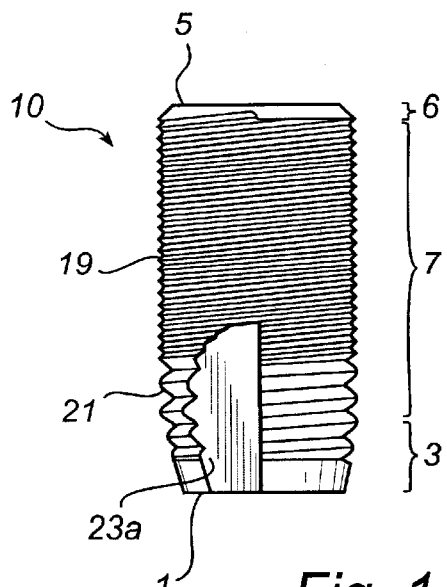
FIG. 1 is a side view of the dental implant.

Referring to FIG. 1, the implant 10 has an apical end 1 which is presented by a first conical section 3 to ease insertion of the implant 10 into the bore-hole, a coronal end 5 presented by a second conical section 6 and an intermediate section 7 of constant diameter which extends between the first and second conical sections 3, 6.

The length of the implant may be in the range 8–19 mm, depending on the clinical situation, and have a maximum outer diameter of 3.5 mm or 4.0 mm. The axial extent of the second conical portion 6 is preferably small compared to the total length of the implant 10, as an example no more than 4.0% perhaps in the range 1.5%–3.7%.

Figure 2:
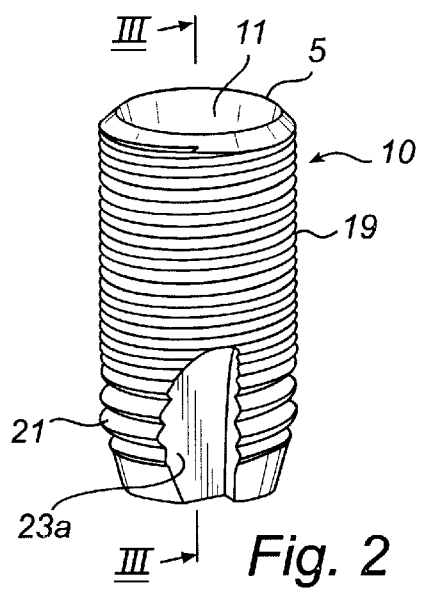
FIG. 2 is a perspective view of the dental implant.
Figure 3:
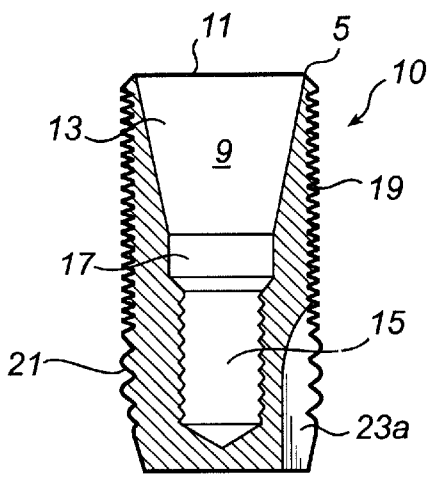
FIG. 3 is a cross-sectional side view of the dental implant.
Figure 4:
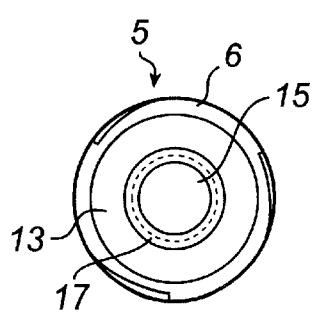
FIG. 4 is a plan view of the dental implant.
Figure 5:
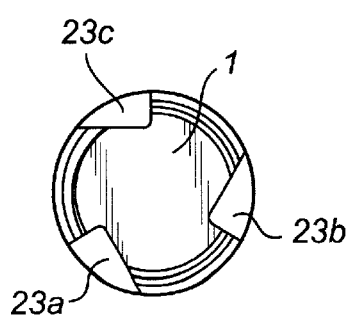
FIG. 5 is an underneath view of the dental implant.
Figure 8:
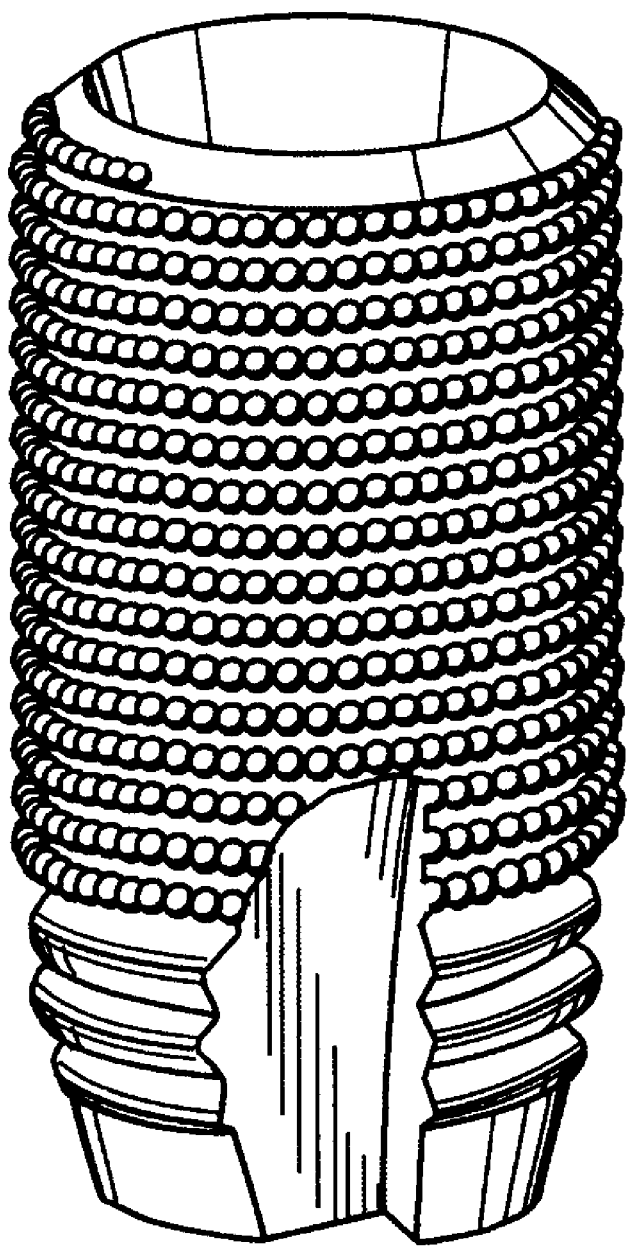
FIG. 8 is a perspective view of a dental implant having circumferentially-oriented roughness consisting of axially spaced, cirucmferential lines of beads.
Figure 9:
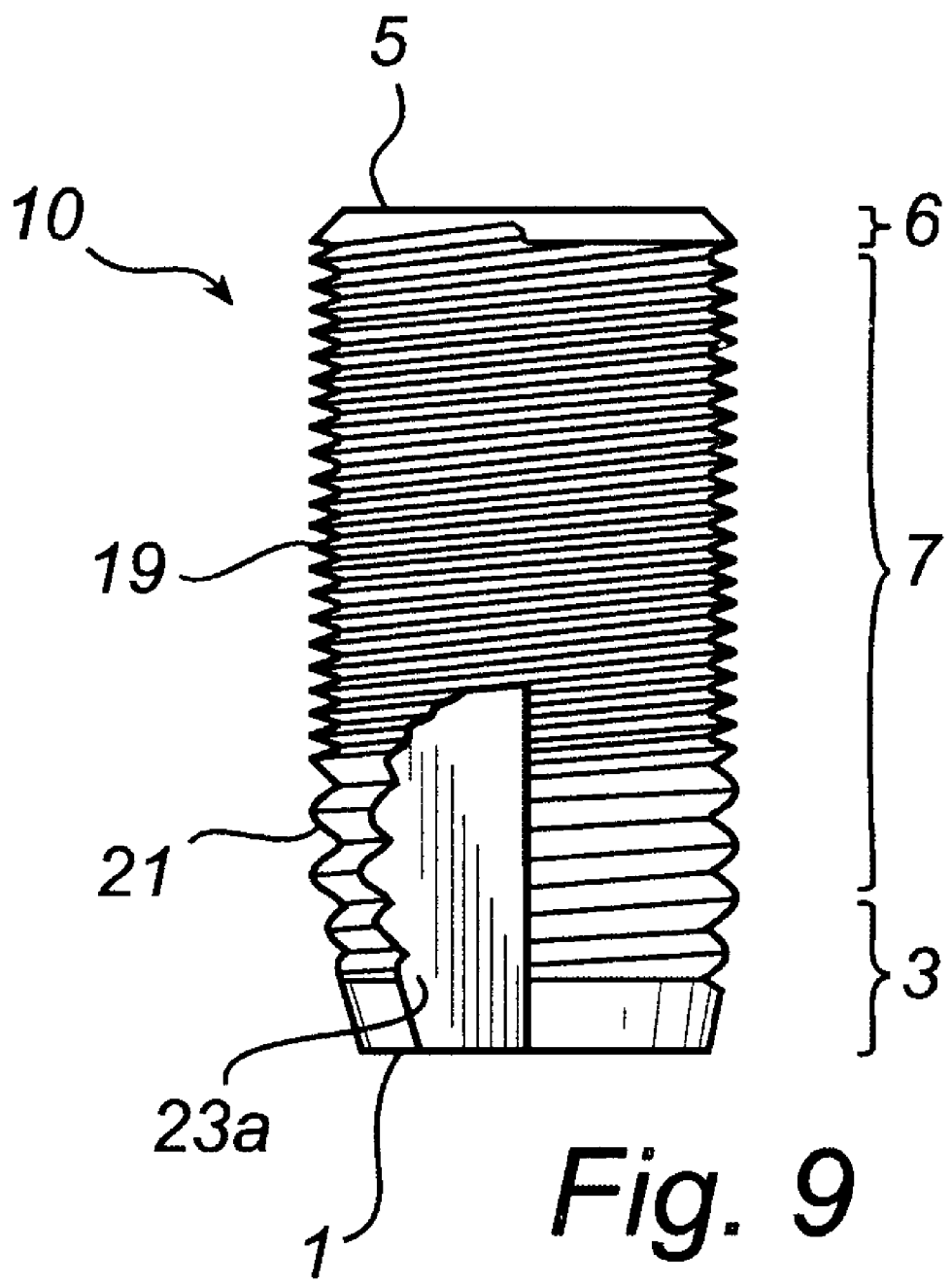
FIG. 9 is a perspective view of a dental implant having circumferentially-oriented roughness in which the height of the peaks in the first axial section and the height of the peaks in the second axial section is the same.

Turning to FIGS. 2 to 4, a socket 9 having an open end 11 in the coronal end 5 extends apically into the implant 10. The socket 9 is for receiving an abutment structure (not shown) which will bridge the gingiva overlying the bore-hole and support/present the prosthetic part. The socket 9 consists of a conical coronal section 13, an internally-threaded apical section 15 and a cylindrical intermediate section 17. The abutment structure will have an apical section which is able to be screw retained in the implant socket 9 for releasably securing the abutment structure to the implant 10. As shown in FIGS. 1 to 3, 6 and 7, the outer surface of the implant 10 over the major part of its length is provided with screw threading which is divided into coronal and apical sections 19, 21 having different thread heights h1, h2. As shown most dearly in FIG. 1, the coronal section 19 of screw threading is positioned on the intermediate cylindrical section 7 of the implant 10 whereas the apical section 21 of the screw threading bridges the intermediate cylindrical section 7 and the first conical section 3.

Referring to FIG. 6, the screw threading in the coronal section 19 is composed of a series of axially spaced-apart screw thread elements each having the same height h1. These screw thread elements are formed by the turns of three separate microthreads (triple microthread) which are sequentially arranged. This means that a screw thread element formed by a first turn of one of the microthreads is axially spaced from a screw thread element formed by the next turn of that microthread by two other screw thread elements, each being respectively formed by a turn of the other two microthreads. A screw thread element belonging to one of the microthreads is therefore axially spaced from the next adjacent screw thread element formed by the same microthread by screw thread elements from each of the other two microthreads. By "microthread" is meant a screw thread having a height which is no greater than 0.2 mm. Accordingly, the screw thread elements in the coronal section 19 have a height h1 which is no greater than 0.2 mm, preferably 0.1 mm.

Referring to FIG. 7, the screw threading in the apical section 21 is composed of a series of axially spaced-apart screw thread elements which, other than those in the first conical section 3, each have the same height h2. The screw thread elements of the apical section 21 are formed by the turns of a single macrothread. By "macrothread" is meant a screw thread having a height greater than 0.2 mm. Accordingly, the screw thread elements of the apical section 21 on the intermediate section 7 have a height greater than 0.2 mm, preferably 0.3 mm.

The angle formed between the coronal and apical flanks of adjacent screw thread elements is the same in both the coronal and apical sections 19, 21. Preferably the angle formed is 80°. It will also be noted from FIGS. 6 and 7 that the coronal and apical flanks of adjacent screw thread elements in the coronal and apical sections 19, 21 are connected by a curved surface, that is to say, there is no axial straight part in-between adjacent screw thread elements in the coronal and apical sections 19, 21.

As can be seen particularly from FIGS. 1 and 3, the tips of the screw thread elements of the coronal section 19 and the tips of the screw thread elements of the apical section 21 positioned in the intermediate cylindrical section 7 of the implant 10 all lie on a common plane when viewed in side section and circumscribe the circumference of the cylindrical intermediate section 7. In other words, the major diameter of the intermediate cylindrical section 7 is constant.

As shown in FIGS. 6 and 7, as well as the screw thread elements in the coronal and apical sections 19, 21 having different heights from one another the crest-to-crest spacing between adjacent screw thread elements in the coronal section 19 is different from the crest-to-crest spacing between adjacent screw thread elements in the apical section 21. The crest-to-crest spacing in the coronal section 19 is d whereas the crest-to-crest spacing in the apical section 21 is 3d. As an example, d may be 0.22 mm. In the case where h1 is 0.1 mm and h2 is 0.3 mm the ratio of the inter-crest spacing to the height would thus be the same for both the coronal and apical threaded sections 19, 21, namely d/h1=2.2=3d/h2.

It follows from the above that the crest-to-crest spacing between adjacent screw thread elements of each microthread is the same as that between adjacent screw thread elements of the macrothread, namely 3d. The fact that the crest-to-crest spacing between adjacent screw thread elements per se in the coronal section 19 is less than that in the apical section 21 is, of course, due to adjacent turns of each microthread being interspersed with a turn from each of the other two microthreads. It will also be noted from FIG. 1 that the turns of the microthreads and the macrothreads are aligned parallel with one another at an inclined angle to the rotational axis of the implant 10.

It will be gathered from the above that the pitch of the coronal and apical threaded sections, 19, 21 will be the same, again being 3d. For this reason, the pitch of the implant 10 remains uniform along its length notwithstanding the difference in crest-to-crest spacing in the apical and coronal threaded sections 19, 21, that is to say, the coronal and apical screw threaded sections 19, 21 will both produce the same axial displacement of the implant 10 when being screwed into the bore-hole provided therefor at the toothless site in the maxilla or mandible. If the coronal and apical sections 19, 21 did not have constant pitch then a greater force would need to be applied to insert the implant 10 into the bore-hole resulting in bone threads formed in the boundary wall of the bore-hole being fractured.

As a rule, a constant pitch for two threaded sections having different crest-to-crest spacings between the adjacent screw thread elements thereof will result where the first threaded section is formed by the sequential arrangement of the turns of a first set of screw threads each having the same pitch and the second threaded section is formed by (i) a single screw thread having the same pitch as the screw threads in the first threaded section, or (ii) the sequential arrangement of the turns of a second set of screw threads numbering less than in the first set each having the same pitch as the screw threads in the first threaded section. The number of screw threads in the first threaded section does not need to be a multiple integer of the number of screw threads in the second threaded section, as in the illustrated embodiment of the invention. For example, there could be five microthreads in the coronal section 19 and two macrothreads in the apical section 21.

As shown in FIGS. 1 to 3 and 5, the implant 10 has three cutting recesses or grooves 23a, 23b, 23c positioned symmetrically about the circumference of the apical end 1 of the implant 10 for self-tapping of the implant 10 when being screwed into the bore-hole provided therefor in the maxilla or mandible. In use, the implant 10 is screwed into the bore-hole provided at the toothless-site in the maxilla or mandible such that the coronal and apical sections 19, 21 are embedded in bone tissue with the second conical section 6 protruding from the maxilla or mandible. The screw thread elements of the macrothreads in the apical section 21 of the implant 10 act to provide primary fixation of the implant in the bore-hole. The screw thread elements of the microthreads in the coronal section 19 also act to provide fixation for the implant 10 in the bore-hole. As a result of the screw threads in the coronal section 19 being microthreads, though, the implant 10 is stiffer than it would be if the screw threads were macrothreads as in the apical section 21. This enables the implant 10 to transfer loads more evenly to the bone tissue adjacent the implant 10 and consequently promote better remodelling of the bone tissue into apposition with the implant 10. Moreover, as the microthreads are positioned at the coronal end 5 of the implant 10 the loads transferred thereby helps alleviate the problem of bone tissue resorption at the coronal surface of the maxilla or mandible (marginal bone tissue resorption).

The provision of microthreads in the coronal section 19 also enables a reasonable wall thickness to be retained around the tapered coronal section 13 of the socket 9 in the implant 10, when compared to the wall thickness that would result from use of macrothreads in the coronal section 19 in any event. This helps preserve the mechanical strength of the implant 10.

To conclude, the dental implant 10 has a screw threaded outer surface 19, 21 which (i) makes it straightforward for the implant 10 to be screwed into a bone tissue structure, and (ii) promotes the short- and long-term stability of the implant 10 in the bone tissue structure.

It will be appreciated that the invention has been illustrated with reference to an exemplary embodiment and that the invention can be varied in many different ways within the scope of the appended claims. As an example, although the illustrated example is a dental implant the invention has equal application in other areas, for example, the orthopaedic area.

Finally, it is to be noted that the inclusion in the appended claims of reference numerals used in the figures of drawings is purely for illustrative purposes and not to be construed as having a limiting effect on the scope of the claims.

What is claimed is:

1. A dental implant comprising a shaft having a coronal end, an apical end, and an outer surface provided with a circumferentially-oriented roughness having a first axial section and a second axial section,
   wherein the implant is sized and configured to be implanted in a maxilla or mandible of a human patient,
   wherein the first axial section is located coronally of the second axial section and the sections of circumferentially-oriented roughness have the same or substantially the same pitch,
   wherein each of the sections comprises a series of circumferentially-oriented peaks, each peak having a crest and being axially spaced apart from adjacent peaks by troughs,
   wherein the axial spacing between the crests of adjacent peaks in the first axial section is less than the axial spacing between the crests of adjacent peaks in the second axial section,
   wherein the crests of all of the peaks or substantially all of the peaks in the first and second axial sections lie on an axial plane parallel to the main axis of the shaft and
   wherein a bore comprising an internally-threaded section extends apically into the shaft from the coronal end.

2. The implant according to claim 1, wherein the first and second axial sections are contiguous.

3. The implant according to claim 2, wherein the first axial section extends from the coronal end of the shaft to a position coronally of the apical end and the second axial section extends from the first axial section towards the apical end.

4. The implant according to any one of claims 1, 2 and 3 wherein the bore extends to an end surface in-between the apical and coronal ends of the shaft, wherein the structure of the end-surface is sized and configured to be secured to a superstructure, wherein the internally-threaded section has a coronal edge and an apical edge for screw connection of the superstructure to the implant, and wherein the apical edge of the internally-threaded section of the bore terminates at a position which is disposed apically of the first axial section.

5. The implant according to claim 4 wherein the internally-threaded section is an apical section of the blind-bore.

6. The implant according to claim 1, wherein the pitch is a predetermined distance and the ratio of the predetermined distance to the axial spacing between the crests of adjacent peaks in the first axial section is a first multiple integer, the ratio of the predetermined distance to the axial spacing between the crests of adjacent peaks in the second axial section is a second multiple integer and the first multiple integer is greater than the second multiple integer.

7. The implant according to claim 1 or 6, wherein the height of the peaks, as measured from the troughs to the crests, in the first axial section differs from that in the second axial section.

8. The implant according to claim 7, wherein the height of the peaks in the first axial section is less than the height of the peaks in the second axial section.

9. The implant according to claim 1 or 6, wherein the height of the peaks, as measured from the troughs to the crests, in the first axial section is the same or substantially the same as in the second axial section.

10. The implant according to claim 1 or 6, wherein the ratio of the height of the peaks, as measured from the troughs to the crests, to the axial spacing between the crests of adjacent peaks in the first axial section is the same or substantially the same as in the second axial section.

11. The implant according to claim 1 or 6, wherein the height of the peaks, as measured from the troughs to the crests, in the first axial section is no greater than 0.20 mm.

12. The implant according to claim 1 or 6, wherein the height of the peaks, as measured from the troughs to the crests, in the second axial section is in the range 0.15–1 mm.

13. The implant according to claim 1 or 6, wherein the circumferentially-oriented roughness in at least one of the first and second axial sections is presented by a screw thread profile with the circumferentially-oriented peaks being defined by thread elements of the screw thread profile.

14. The implant according to claim 13, wherein the screw thread profile is formed by a screw thread structure.

15. The implant according to claim 13 wherein both the first and second axial sections are presented by a screw thread profile with the circumferentially-oriented peaks being defined by thread elements of the screw thread profiles.

16. The implant according to claim 15, wherein the screw thread profile of the first axial section is formed by a first set of at least two independent screw threads each screw thread forming turns, the turns of each independent screw thread in the first set defining thread elements in the first axial section and being alternately arranged with the screw thread elements of the other independent screw threads in the first set, wherein adjacent screw thread elements of any of the independent screw threads of the first set are axially spaced apart from each other by a predetermined spacing distance, wherein the spacing distance is the same for the adjacent screw thread elements of the other independent screw threads in the first set, and wherein, the screw thread profile of the second axial section is formed by (i) a single screw thread having turns which define the thread elements of the second axial section and are axially spaced apart from each other by the predetermined spacing distance or approximately the predetermined spacing distance, or (ii) a second set of independent screw threads numbering less than in the first set, each screw thread having turns, the turns of each independent screw thread in the second set defining screw thread elements in the second axial section, the screw thread elements of one independent screw thread of the second set being alternately arranged with the screw thread elements of the other independent screw threads in the second set with adjacent screw thread elements of each independent screw thread of the second set being axially spaced apart from each other by the predetermined spacing distance or approximately the predetermined spacing distance.

17. The implant according to claim 16, wherein at least one of the independent screw threads of the first and second axial sections is shared by the first and second axial sections.

18. The implant according to claim 16, wherein the or each independent screw thread of at least one of the first and second axial sections is a microthread.

19. The implant according to claim 18, wherein only the independent screw threads of the first axial section are microthreads.

20. The implant according to claim 18, wherein the independent screw threads of the first and second axial sections are microthreads.

21. The implant according to claim 1 or 6, wherein the circumferentially-oriented roughness in at least one of the first and second axial sections is formed by a series of axially spaced apart circumferential lines of beads.

22. The implant according to claim 21, wherein the beads in each line are circumferentially spaced apart.

23. The implant according to claim 1, wherein the height (h1, h2) of the peaks, as measured from the troughs to the crests, in the first axial section differs from that in the second axial section.

24. The implant according to claim 1, wherein the height (h1, h2) of the peaks, as measured from the troughs to the crests, in the first axial section is the same or substantially the same as in the second axial section.

25. The implant according to claim 1, wherein the ratio of the height of the peaks, as measured from the troughs to the crests, to the axial spacing between the crests of adjacent peaks in the first axial section is the same or substantially the same as in the second axial section.

26. The implant according to claim 1, wherein the circumferentially-oriented roughness consists of a first axial section and a second axial section.

27. An implant comprising a shaft, wherein the shaft is sized and configured to be embedded in bone tissue and comprises a coronal end having a coronal end portion with a maximum lateral dimension not exceeding the maximum lateral dimension of the shaft, an apical end, and an outer surface having at least two axial sections having circumferentially-oriented roughness, each of the sections comprising a series of circumferentially-oriented peaks, each peak having a crest and being axially spaced apart from adjacent peaks by troughs, wherein the axial spacing between the crests of adjacent peaks of a section is less than the axial spacing between the crests of adjacent peaks of any apically-located axial section, wherein the sections of circumferentially-oriented roughness have the same or substantially the same pitch, and wherein the crests of all of the peaks or substantially all of the peaks in the first and second axial sections lie on an axial plane parallel to the main axis of the shaft.

28. The implant according to claim 27, wherein at least two of the axial sections are contiguous.

29. The implant according to claim 27, wherein a blind bore extends apically into the shaft from the coronal end to an end surface in-between the apical and coronal ends of the shaft, wherein the structure of the end-surface is capable of being secured to a superstructure, wherein the blind bore comprises an internally-threaded section having a coronal edge and an apical edge for screw connection of the superstructure to the implant, and wherein the apical edge of the internally-threaded section of the blind bore terminates at a position which is disposed apically of the first axial section of the at least two axial sections.

30. The implant according to claim 27, wherein for at least one pair of the axial sections, a first axial section being located coronally of a second axial section, the pitch is a predetermined distance, that the ratio of the predetermined distance to the axial spacing between the crests of adjacent peaks in the first axial section is a first multiple integer, that the ratio of the predetermined distance to the axial spacing between the crests of adjacent peaks in the second axial section is a second multiple integer and that the first multiple integer is greater than the second multiple integer.

31. The implant according to claim 30, the height of the peaks, as measured from the troughs to the crests, in the first axial section differs from that in the second axial section.

32. The implant according to claim 31, wherein the height of the peaks in the first axial section is less than the height of the peaks in the second axial section.

33. The implant according to claim 30, wherein the height of the peaks, as measured from the troughs to the crests, in the first axial section is the same or substantially the same as in the second axial section.

34. The implant according to claim 30, wherein the ratio of the height of the peaks, as measured from the troughs to the crests, to the axial spacing between the crests of adjacent peaks in the first axial section is the same or substantially the same as in the second axial section.

35. The implant according to claim 30, wherein the height of the peaks, as measured from the troughs to the crests, in the first axial section is no greater than 0.20 mm.

36. The implant according to claim 30, wherein the height of the peaks, as measured from the troughs to the crests, in the second axial section is in the range 0.15–1 mm.

37. The implant according to claim 30, wherein the circumferentially-oriented roughness in at least one of the first and second axial sections is presented by a screw thread profile with the circumferentially-oriented peaks being defined by thread elements of the screw thread profile.

38. The implant according to claim 37, wherein both the first and second axial sections are presented by a screw thread profile wherein the circumferentially-oriented peaks are defined by screw thread elements of the screw thread profiles, wherein the screw thread profile of the first axial section is formed by a first set of at least two independent screw threads, each screw thread having turns, the turns of each independent screw thread in the first set defining thread elements in the first axial section and being alternately arranged with the screw thread elements of the other independent screw threads in the first set, wherein adjacent screw thread elements of each one of the independent screw threads of the first set are axially spaced apart from each other by a predetermined spacing distance, wherein the spacing distance is the same for the adjacent screw thread elements of the other independent screw threads in the first set, and wherein, the screw thread profile of the second axial section is formed by (i) a single screw thread having turns which define the screw thread elements of the second axial section and are axially spaced apart from each other by the predetermined spacing distance or approximately the predetermined spacing distance, or (ii) a second set of independent screw threads numbering less than in the first set, each having turns, the turns of each independent screw thread in the second set defining screw thread elements in the second axial section, the screw thread elements of one independent screw thread of the second set being alternately arranged with the screw thread elements of the other independent screw threads of the second set with adjacent screw thread elements of each independent screw thread of the second set being axially spaced apart from each other by the predetermined spacing distance or approximately the predetermined spacing distance.

39. The implant according to claim 27, wherein the implant is sized and configured to be implanted in a maxilla or a mandible of an edentulous patient for supporting a superstructure which presents one or more artificial teeth.

40. An implant comprising a shaft, wherein the shaft is sized and configured to be embedded in bone tissue and comprises a coronal end having a coronal end portion with a maximum lateral dimension not exceeding the maximum lateral dimension of the shaft an apical end, and an outer surface provided with a circumferentially-oriented roughness consisting of a first axial section and a second axial section, each of the sections comprising a series of circumferentially-oriented peaks, each peak having a crest and being axially spaced apart from adjacent peaks by troughs, wherein the axial spacing between the crests of adjacent peaks in the first axial section is less than the axial spacing between the crests of adjacent peaks in the second axial section, wherein the first and second axial sections of circumferentially-oriented roughness have the same or substantially the same pitch, wherein the first axial section is located coronally of the second axial section, and wherein the crests of all of the peaks or substantially all of the peaks in the first and second axial sections lie on an axial plane parallel to the main axis of the shaft.

41. The implant according to claim 40, wherein the first and second axial sections are contiguous.

42. The implant according to claim 40, wherein a blind bore extends apically into the shaft from the coronal end to an end surface in-between the apical and coronal ends of the shaft, wherein the structure of the end-surface is capable of being secured to a superstructure, wherein the blind bore comprises an internally-threaded section having a coronal edge and an apical edge for screw connection of the superstructure to the implant, and wherein the apical edge of the internally-threaded section of the blind bore terminates at a position which is disposed apically of the first axial section.

43. The implant according to claim 40, wherein the pitch is a predetermined distance, that the ratio of the predetermined distance to the axial spacing between the crests of adjacent peaks in the first axial section is a first multiple integer, that the ratio of the predetermined distance to the axial spacing between the crests of adjacent peaks in the second axial section is a second multiple integer and that the first multiple integer is greater than the second multiple integer.

44. The implant according to claim 40 or 43, wherein the height of the peaks, as measured from the troughs to the crests, in the first axial section differs from that in the second axial section.

45. The implant according to claim 44, wherein the height of the peaks in the first axial section is less than the height of the peaks in the second axial section.

46. The implant according to claim 40 or 43, wherein the height of the peaks, as measured from the troughs to the crests, in the first axial section is the same or substantially the same as in the second axial section.

47. The implant according to claim 40 or 43, wherein the ratio of the height of the peaks, as measured from the troughs to the crests, to the axial spacing between the crests of adjacent peaks in the first axial section is the same or substantially the same as in the second axial section.

48. The implant according to claim 40 or 43, wherein the height of the peaks, as measured from the troughs to the crests, in the first axial section is no greater than 0.20mm.

49. The implant according to claim 40 or 43, wherein the height of the peaks, as measured from the troughs to the crests, in the second axial section is in the range 0.15–1 mm.

50. The implant according to claim 40 or 43, wherein the circumferentially-oriented roughness in at least one of the first and second axial sections is presented by a screw thread profile with the circumferentially-oriented peaks being defined by thread elements of the screw thread profile.

51. The implant according to claim 50, wherein both the first and second axial sections are presented by a screw thread profile wherein the circumferentially-oriented peaks are defined by screw thread elements of the screw thread profiles, wherein the screw thread profile of the first axial section is formed by a first set of at least two independent screw threads each screw thread forming turns, the turns of each independent screw thread in the first set defining screw thread elements in the first axial section and being alternately arranged with the screw thread elements of the other independent screw threads in the first set, wherein adjacent screw thread elements of each of the independent screw threads of the first set are axially spaced apart from each other by a predetermined spacing distance, wherein the spacing distance is the same for the adjacent screw thread elements of the other independent screw threads in the first set, and wherein, the screw thread profile of the second axial section is formed by (i) a single screw thread having turns which define the thread elements of the second axial section and are axially spaced apart from each other by the predetermined spacing distance or approximately the predetermined spacing distance, or (ii) a second set of independent screw threads numbering less than in the first set, each screw thread forming turns, the turns of each independent screw thread in the second set defining screw thread elements in the second axial section and being alternately arranged with the screw thread elements of the other independent screw threads in the second set, with adjacent screw thread elements of each independent screw thread of the second set being axially spaced apart from each other by the predetermined spacing distance or approximately the predetermined spacing distance.

52. The implant according to claim 40, the implant is sized and configured to be implanted in a maxilla or a mandible of an edentulous patient for supporting a superstructure which presents one or more artificial teeth.

53. An implant comprising a shaft sized and configured to be embedded in a maxilla or mandible, wherein the shaft comprises a coronal end, an apical end, and an outer surface having a plurality of axial sections having circumferentially-oriented roughness and the sections of circumferentially-oriented roughness have the same or substantially the same pitch, each of the sections comprising a series of circumferentially-oriented peaks, each peak having a crest and being axially spaced apart from adjacent peaks by troughs, wherein the axial spacing between the crests of adjacent peaks of a section is less than the axial spacing between the crests of adjacent peaks of the adjacent apically-located axial section, wherein the crests of all of the peaks or substantially all of the peaks in at least two of said sections lie on an axial plane parallel to the main axis of the shaft, and wherein a bore comprising an internally-threaded section extends apically into the shaft from the coronal end.

54. The implant according to claim 53, wherein the crests of all of the peaks, or substantially all of the peaks, in all of said axial sections lie on an axial plane parallel to the main axis of the shaft.

55. The implant according to claim 54, wherein the height (h1, h2) of the peaks, as measured from the troughs to the crests, in the first axial section differs from that in the second axial section.

56. The implant according to claim 54, wherein the height (h1, h2) of the peaks, as measured from the troughs to the crests, in the first axial section is the same or substantially the same as in the second axial section.

57. The implant according to claim 54, wherein the ratio of the height of the peaks, as measured from the troughs to the crests, to the axial spacing between the crests of adjacent peaks in the first axial section is the same or substantially the same as in the second axial section.

58. A dental implant comprising a shaft having a coronal end, an apical end, and an outer surface provided with a circumferentially-oriented roughness having a first axial section and a second axial section, wherein the implant is sized and configured to be implanted in a maxilla or mandible of a human patient, wherein the first axial section is located coronally of the second axial section and the sections of circumferentially-oriented roughness have the same or substantially the same pitch, wherein each of the sections comprises a series of circumferentially-oriented peaks, each peak having a crest and being axially spaced apart from adjacent peaks by troughs, and wherein the axial spacing between the crests of adjacent peaks in the first axial section is less than the axial spacing between the crests of adjacent peaks in the second axial section, wherein the crests of all of the peaks or substantially all of the peaks in the first and second axial sections lie in an axial plane parallel to the main axis of the shaft, and wherein a bore extends apically into the shaft from the coronal end and terminates at a position disposed apically from the first axial section.

59. The implant according to claim 58, wherein the first and second axial sections are contiguous.

60. The implant according to claim 59, wherein the first axial section extends from the coronal end of the shaft to a position coronally of the apical end and the second axial section extends from the first axial section towards the apical end.

61. The implant according to any one of claim 58–60, wherein the bore extends to an end surface in-between the apical and coronal ends of the shaft, wherein the structure of the end-surface is capable of being secured to a superstructure, wherein the bore comprises an internally-threaded section having a coronal edge and an apical edge for screw connection of the superstructure to the implant, and wherein the apical edge of the internally-threaded section of the bore terminates at a position which is disposed apically of the first axial section.

62. The implant according to claim 61, wherein the internally-threaded section is an apical section of the bore.

63. The implant according to claim 94, wherein the pitch is a predetermined distance and the ratio of the predetermined distance to the axial spacing between the crests of adjacent peaks in the first axial section is a first multiple integer, the ratio of the predetermined distance to the axial spacing between the crests of adjacent peaks in the second axial section is a second multiple integer and the first multiple integer is greater than the second multiple integer.

64. The implant according to claim 58–63, wherein the height of the peaks, as measured from the troughs to the crests, in the first axial section differs from that in the second axial section.

65. The implant according to claim 64, wherein the height of the peaks in the first axial section is less than the height of the peaks in the second axial section.

66. The implant according to claim 58 or 63 the height of the peaks, as measured from the troughs to the crests, in the first axial section is the same or substantially the same as in the second axial section.

67. The implant according to claim 58 or 63, wherein the ratio of the height.of the peaks, as measured from the troughs to the crests, to the axial spacing between the crests of adjacent peaks in the first axial section is the same or substantially the same as in the second axial section.

68. The implant according to claim 58 or 63, wherein the height of the peaks, as measured from the troughs to the crests, in the first axial section is no greater than 0.20 mm.

69. The implant according to claim 58 or 63, wherein the height of the peaks, as measured from the troughs to the crests, in the second axial section is in the range 0.15–1 mm.

70. The implant according to claim 58 or 63, wherein the circumferentially-oriented roughness in at least one of the first and second axial sections is presented by a screw thread profile with the circumferentially-oriented peaks being defined by thread elements of the screw thread profile.

71. The implant according to claim 70 wherein both the first and second axial sections are presented by a screw thread profile with the circumferentially-oriented peaks being defined by thread elements of the screw thread profiles.

72. The implant according to claim 70, wherein the or each screw thread profile is formed by a screw thread structure.

73. The implant according to claim 71, wherein the or each screw thread profile is formed by a screw thread structure.

74. The implant according to claim 73, wherein the screw thread profile of the first axial section is formed by a first set of independent screw threads each screw thread having turns, the turns of each independent screw thread in the first set defining thread elements in the first axial section and being sequentially arranged with the turns of the other independent screw threads in the first set with adjacent turns of one of the independent screw threads of the first set being axially spaced apart by a predetermined spacing distance which is the same for adjacent turns of the other independent screw threads in the first set, and wherein the screw thread structure of the second axial section is formed by (i) an independent screw thread having turns which define the thread elements of the second axial section and are axially spaced apart by the predetermined spacing distance or essentially the predetermined spacing distance, or (ii) a second set of independent screw threads numbering less than in the first set each having turns, the turns of each independent screw thread in the second set defining thread elements in the second axial section and being sequentially arranged with the turns of the other independent screw threads in the second set with adjacent turns of each independent screw thread of the second set being axially spaced apart by the predetermined spacing distance or a distance approximating the predetermined spacing distance.

75. The implant according to claim 74, wherein at least one of the independent screw threads of the first and second axial sections is shared by the first and second axial sections.

76. The implant according to claim 74, wherein the or each independent screw thread of at least one of the first and second axial sections is a microthread.

77. The implant according to claim 76, wherein only the independent screw threads of the first axial section are microthreads.

78. The implant according to claim 76, wherein the independent screw threads of the first and second axial sections are microthreads.

79. The implant according to claim 58 or 63, wherein the circumferentially-oriented roughness in at least one of the first and second axial sections is formed by a series of axially spaced apart circumferential lines of beads.

80. The implant according to claim 79, wherein the beads in each line are circumferentially spaced apart.

81. The implant according to claim 58, wherein the circumferentially-oriented roughness consists of a first axial section and a second axial section.

82. A method of implanting an implant into a bone structure comprising the steps of:
   providing an implant according to any one of claims 1, 6, 27, 40, 53, and 58:
   providing a bore-hole in the bone tissue structure; and
   screwing the implant into the bore-hole so that the shaft is embedded in the bone tissue.

* * * * *

UNITED STATES PATENT AND TRADEMARK OFFICE
CERTIFICATE OF CORRECTION

PATENT NO. : 6,547,564 B1
DATED : April 15, 2003
INVENTOR(S) : Stig Hansson

It is certified that error appears in the above-identified patent and that said Letters Patent is hereby corrected as shown below:

Column 12,
Line 31, replace "shaft" with -- shaft, --.

Column 13,
Line 28, after "58 or 63" insert -- wherein --.
Line 33, replace "height.of" with -- height of --.
Line 66, after "claim 40" insert -- wherein --.

Column 15,
Line 13, replace "94" with -- 58 --.
Line 21, replace "58-63" with -- 58 or 63 --.

Signed and Sealed this

Ninth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,547,564 B1
DATED          : April 15, 2003
INVENTOR(S)    : Stig Hansson It is certified that error appears in the above-identified patent and that said Letters Patent is hereby corrected as shown below:

<u>Column 12,</u>
Line 31, replace "shaft" with -- shaft, --.

<u>Column 13,</u>
Line 66, after "claim 40" insert -- wherein --.

<u>Column 15,</u>
Line 13, replace "94" with -- 58 --.
Line 21, replace "58-63" with -- 58 or 63 --.
Line 28, after "58 or 63" insert -- wherein --.
Line 33, replace "height.of" with -- height of --.

This certificate supersedes Certificate of Correction issued September 9, 2003.

Signed and Sealed this

Thirtieth Day of December, 2003

JAMES E. ROGAN
*Director of the United States Patent and Trademark Office*